(12) United States Patent
Harder et al.

(10) Patent No.: US 10,639,207 B1
(45) Date of Patent: May 5, 2020

(54) MEDICAL DRESSING TO TREAT SUCKING CHEST WOUND

(71) Applicant: H&H Medical Corporation, Williamsburg, VA (US)

(72) Inventors: Paul X. Harder, Williamsburg, VA (US); John Biddle, Williamsburg, VA (US); Jeffrey B. Gray, Williamsburg, VA (US)

(73) Assignee: H&H Medical Corporation, Williamsburg, VA (US)

( * ) Notice: Subject to any disclaimer, the term of this patent is extended or adjusted under 35 U.S.C. 154(b) by 529 days.

(21) Appl. No.: 15/494,111

(22) Filed: Apr. 21, 2017

(51) Int. Cl.
*A61F 13/00* (2006.01)
*A61F 13/02* (2006.01)

(52) U.S. Cl.
CPC ........ *A61F 13/0233* (2013.01); *A61F 13/025* (2013.01); *A61F 2013/00114* (2013.01); *A61F 2013/00246* (2013.01)

(58) Field of Classification Search
None
See application file for complete search history.

(56) References Cited

U.S. PATENT DOCUMENTS

| | | | |
|---|---|---|---|
| 4,465,062 A | 8/1984 | Versaggi et al. | |
| 4,717,382 A | 1/1988 | Clemens et al. | |
| 5,431,633 A | 7/1995 | Fury | |
| 5,478,333 A * | 12/1995 | Asherman, Jr. | ....... A61F 13/143 128/887 |
| 7,504,549 B2 | 3/2009 | Castellani et al. | |
| 8,309,786 B2 | 11/2012 | Scheremet et al. | |
| 8,710,289 B2 | 4/2014 | Russell et al. | |
| 9,000,251 B2 | 4/2015 | Murphy et al. | |
| D766,448 S | 9/2016 | Gergely et al. | |
| 9,452,088 B2 | 9/2016 | Shulman et al. | |
| 10,383,988 B2 * | 8/2019 | Bussett | ................... A61M 1/04 |
| 2007/0232978 A1 * | 10/2007 | Castellani | ............. A61F 13/023 602/41 |

(Continued)

OTHER PUBLICATIONS

Hyfin Vent Chest Seal Twin Pack, www.chinookmed.com, two pages, Mar. 24, 2017.

(Continued)

*Primary Examiner* — Kim M Lewis
(74) *Attorney, Agent, or Firm* — Nixon & Vanderhye P.C.

(57) ABSTRACT

A medical dressing configured to be applied to a chest wound, the dressing including: a flexible main membrane including a front surface configured to face a chest of a patient and a back surface opposite to the front surface, wherein the flexible main membrane includes an opening; an adhesive layer on the front surface of the main membrane wherein the adhesive layer extends entirely around the opening; a flexible sealing membrane entirely covering the opening of the flexible main and overlapping at least a portion of the main membrane; an annular array of joints sandwiched between the sealing membrane and the main membrane, wherein the array of joints extends around the opening; and vent passages sandwiched between the main membrane and the sealing membrane, wherein vent passages each extend between an adjacent pair of the joints and defines an air passage from the opening and to an outer edge of the sealing membrane.

18 Claims, 5 Drawing Sheets

(56) References Cited

U.S. PATENT DOCUMENTS

| | | | |
|---|---|---|---|
| 2007/0244421 A1* | 10/2007 | Graham | A61F 13/00051 |
| | | | 602/43 |
| 2008/0091152 A1* | 4/2008 | Asherman | A61M 1/04 |
| | | | 604/315 |
| 2011/0054340 A1 | 3/2011 | Russ et al. | |
| 2012/0078153 A1 | 3/2012 | Russell et al. | |
| 2015/0320919 A1* | 11/2015 | Bussett | A61M 1/04 |
| | | | 604/540 |
| 2017/0312402 A1* | 11/2017 | McDonald | A61F 13/0216 |

OTHER PUBLICATIONS

Hyfin Vent Chest Seal Twin Pack, www.narescue.com, one page Mar. 24, 2017.

Ronald A. Bergman, "Anatomy Atlases-Sucking Chest Wound", six pages, Mar. 24, 2017.

* cited by examiner

MEDICAL DRESSING TO TREAT SUCKING CHEST WOUND

BACKGROUND OF THE INVENTION

This invention relates to a medical dressing for treating open chest injuries or other injuries that may expose the pleural space or chest cavity.

Chest trauma, including piercing or penetrating chest wounds, can occur as the result of an accidental or deliberate penetration of a foreign object into the body. Risk from chest trauma can be exacerbated if the internal chest volume or lungs are exposed to the external environs ent. Depending on the severity of the trauma, effective triage using specifically adapted medical dressings may greatly minimize the risk of serious consequences including pneumothorax and loss of life.

The lungs are made up of layers of tissue known as pleura and are maintained within an enclosed pleural space, which is naturally maintained at a slight, negative pressure. In the event an individual suffers a puncture wound to the chest, the chest wound may penetrate the chest cavity, exposing the pleural space to the external atmosphere. The exposure of the pleural space may allow air from the atmosphere to flow into the pleura space and raise the pressure in the space as to precipitate lung collapse. This buildup of air pressure in the pleural space can have serious and consequential effects on lung mechanics and can make it difficult for patients to breath. Because the flow of air into the pleural space is typically audible, these types of wounds are commonly referred to as "sucking chest wounds."

If left untreated the buildup of air in the pleural space can quickly result in the recession of the lung, lung collapse, or pneumothorax. A pneumothorax results from the abnormal buildup of air in the pleural space and may manifest as an uncoupling of the lung from the chest wall. Immediate symptoms typically include a sudden onset of sharp chest pain (general one-sided and localized to the side of the wound opening, and shortness of breath. If left untreated, these symptoms may progress to difficulty breathing, or even death.

Generally, the prescribed treatment to a penetrating chest wound, e.g., a sucking chest wound, is to limit air entry into the pleura space by sealing the wound and evacuate air from the pleura space.

BRIEF DESCRIPTION OF THE INVENTION

An invention has been conceived and is disclosed herein for a medical-grade chest seal device, e.g., dressing, with minimized thickness, or low-profile, to treat a puncturing chest wound, lung collapse and open pneumothorax. The chest seal device includes a series, e.g., six or more, of one way passages that allow air to vent from within the chest. Due to the number of one-way passages, air may vent even if one or more of the passages become clogged by clotted blood or other obstructions in the passage. Another advantage of the chest seal is the simplicity of its construction and operation, which makes the seal easy to apply, and not prone to mechanical failure while also maintaining a low cost of manufacture.

A medical dressing has been conceived and is disclosed herein that is configured to be applied to a chest wound, the dressing including: a flexible main membrane including a front surface configured to face a chest of a patient and a back surface opposite to the front surface, wherein the flexible main membrane includes an opening; an adhesive layer on the front surface of the main membrane wherein the adhesive layer extends entirely around the opening; a flexible sealing membrane entirely covering the opening of the flexible main membrane and overlapping at least a portion of the main membrane; an annular array of joints sandwiched between the sealing membrane and the main membrane, wherein the array of joints extends around the opening; and vent passages sandwiched between the main membrane and the sealing membrane, wherein vent passages each extend between an adjacent pair of the joints and defines an air passage from the opening to an outer edge of the sealing membrane.

A medical dressing has been conceived and is disclosed herein that is configured to be applied to a chest wound, the dressing comprising: a flexible main membrane including a front surface configured to face the chest of a patient and a back surface opposite to the front surface, wherein the flexible main membrane includes an opening; an adhesive layer on the front surface of the main membrane wherein the adhesive layer extends entirely around the opening and is offset from the opening by at least one-eighth of an inch; a flexible sealing membrane entirely covering the opening of the flexible main membrane and overlapping at least a portion of the main membrane; an array of joints sandwiched between the sealing membrane and the main membrane, wherein the array of joints extends around the opening of the main membrane, and vent passages sandwiched between the main membrane and the sealing membrane, wherein vent a passage extends between joints in the array of joints and each of the vent passages defines an air passage from the opening and to an outer edge of the sealing membrane.

The medical dressing may include: a flexible flange body having at least two layers having a top side surface and a bottom side surface, said flange body having at least one central opening defined there through in a central portion thereof; a top layer permanently connected or partially sealed along its outer circumference to the bottom layer and a bottom biocompatible layer configured with an adhesive disposed on said bottom surface of said flexible flange body, the top layer further comprising and a seat, which may form a valve, to overlie an annular neck surrounding the central opening of the bottom layer of said flange, said one-way valve comprising a valve body having a peripheral wall or sealing element disposed in said valve body so as to selectively seat to seal said passage to preclude air flow in one direction through said valve body and so as to be selectively unseated to allow flow through said valve body in the opposite direction, and a plurality of passages fluidly connecting the area under the top layer to the external atmosphere, whereby when the flange body is adhered to the skin of a patient with said at least one central opening generally overlying a chest wound, air is allowed to escape from the chest wound through the one-way valve whereas air flow into the chest wound is precluded.

The medical dressing may also be embodied in a method of treating an open pneumothorax comprising: providing a chest seal comprising: a flexible flange body comprised of at least two layers having a top side surface and a bottom side surface, said flange body having at least one central opening defined there through in a central portion thereof; a top layer permanently connected or sealed along its outer circumference to the bottom layer and a bottom biocompatible layer configured with an adhesive disposed on said bottom surface of said flexible flange body, the top layer further comprising and a single one-way valve seated to overlie an annular neck surrounding the central opening of the bottom layer of said flange, said one-way valve comprising a valve body having a peripheral wall or sealing element disposed in said valve body so as to selectively seat to seal said passage to preclude air flow in one direction through said valve body and so as to be selectively unseated to allow flow through said valve body in the opposite direction, and a plurality of passages fluidly connecting the area under the top layer to the external atmosphere, whereby when the flange body is adhered to the skin of a patient with said at least one central opening generally overlying a chest wound, air is allowed to escape from the chest wound through the one-way valve whereas air flow into the chest wound is precluded.

DETAILED DESCRIPTION OF THE INVENTION

Figure 1:
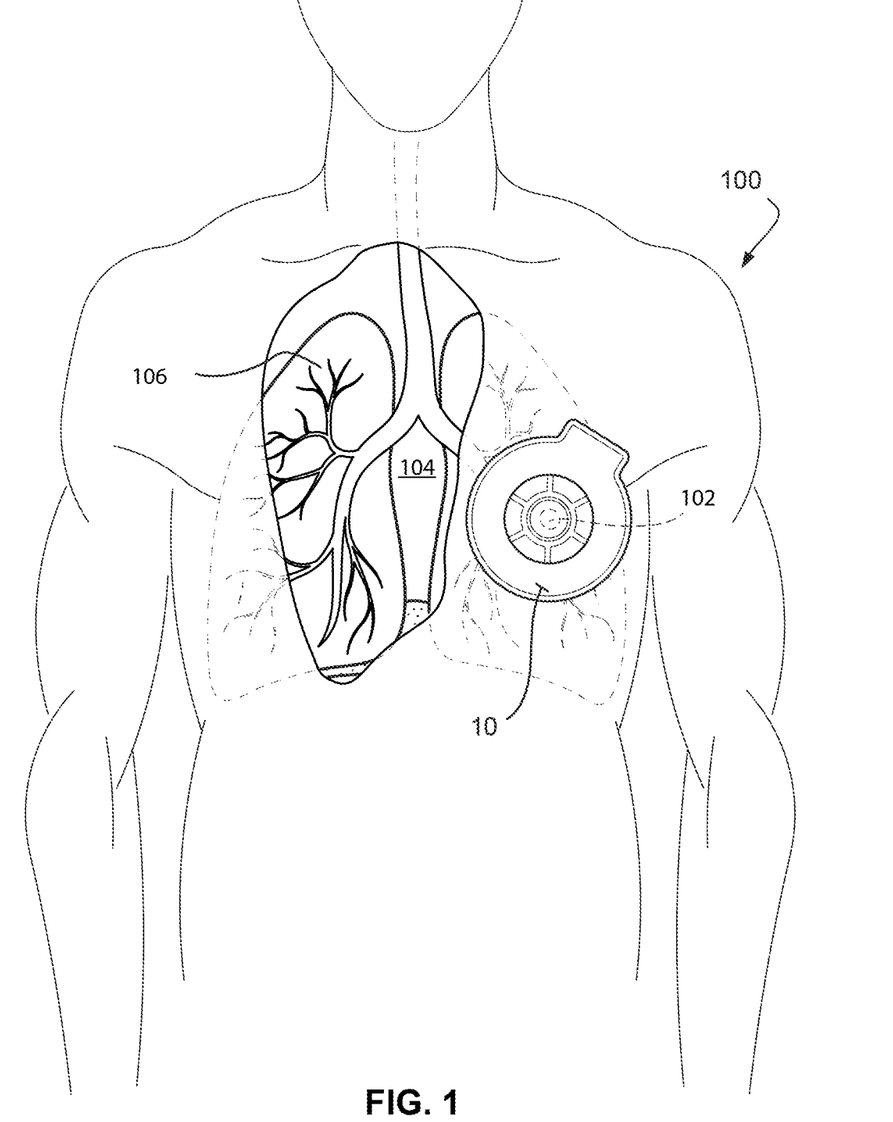
FIG. 1 is a view of a patient with a medical dressing applied to the lower chest or abdomen.

FIG. 1 shows a patient 100 with a chest wound, such as a puncture 102 that extends through the chest wall and to the pleural space such that air flows from the atmosphere to the pleural space 104. Air entering the pleura can collapse the lung(s) 106 of the patient. The sound of air being sucked into the wound typically characterizes this type of wound. These wounds are often referred to as a sucking chest wound. Immediate and emergency treatment of a sucking chest wound involves the application of a dressing to the wound to allow air to vent from the pleura space and prevent additional air from being drawn back into the pleura space.

A medical dressing 10 is applied to the chest puncture 102. The dressing is applied such that the puncture 102 is aligned with the center of the dressing 10. Before the dressing is applied, the wound may be cleaned by removing blood and dirt from the skin surround the wound. An adhesive layer on one side of the dressing seals the dressing to the skin. The dressing covers the puncture 102 to prevent water, dirt and other material from entering the wound. The dressing may also assist in stopping further loss of blood from the wound. The dressing also prevents air from being drawn into the puncture 102 while also allowing air to vent from the puncture and to the atmosphere. A second medical dressing 10 may be applied to the back (not shown) of the patient where there may be an exit (or entrance) wound, especially if the wound is caused by a gunshot.

Figure 2:
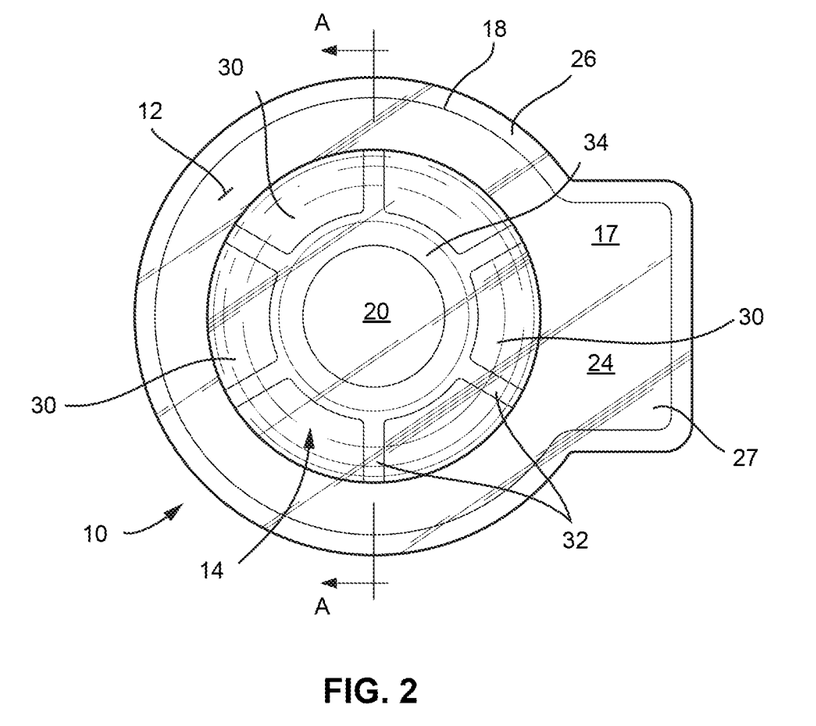
FIG. 2 is a top view of the medical dressing.
Figure 3:
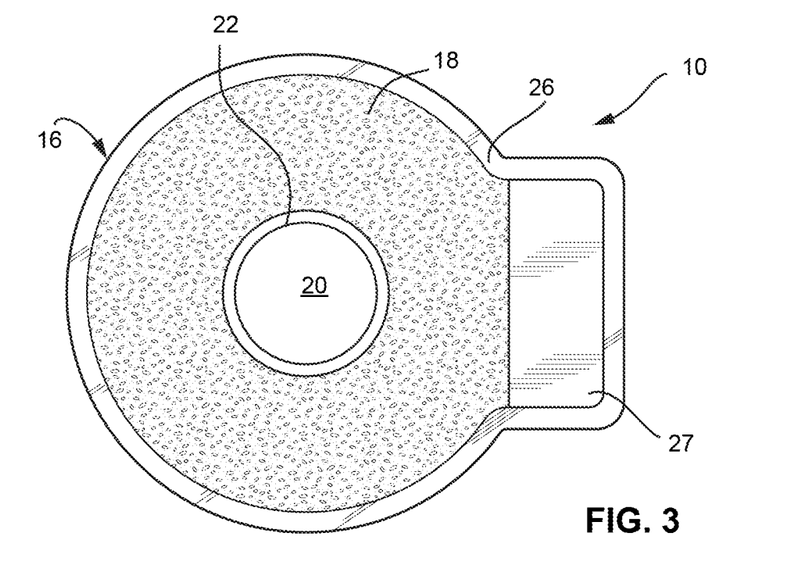
FIG. 3 is the bottom view of the medical dressing, which a release liner removed from the dressing.
Figure 4:
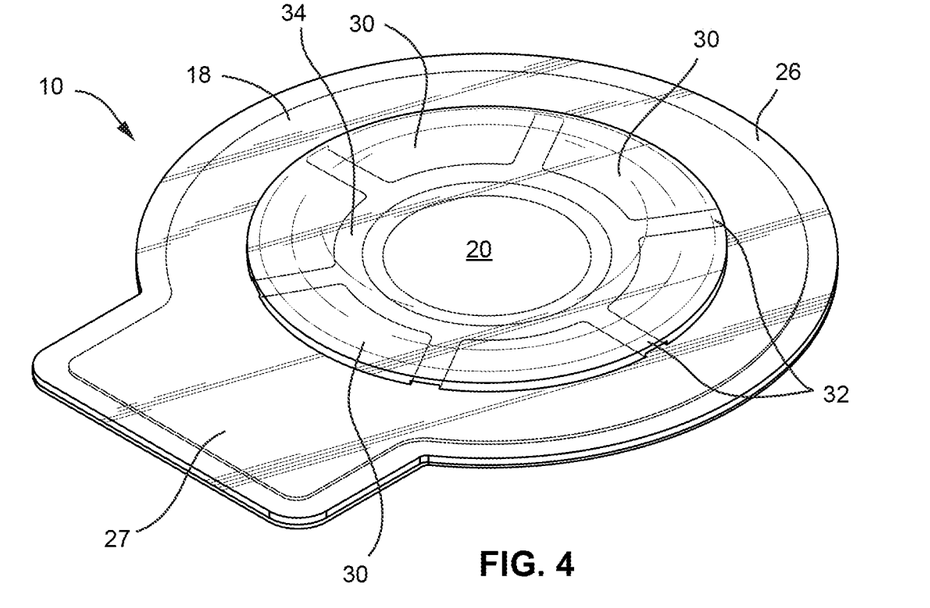
FIG. 4 is a perspective view of the top of the medical dressing.
Figure 5:
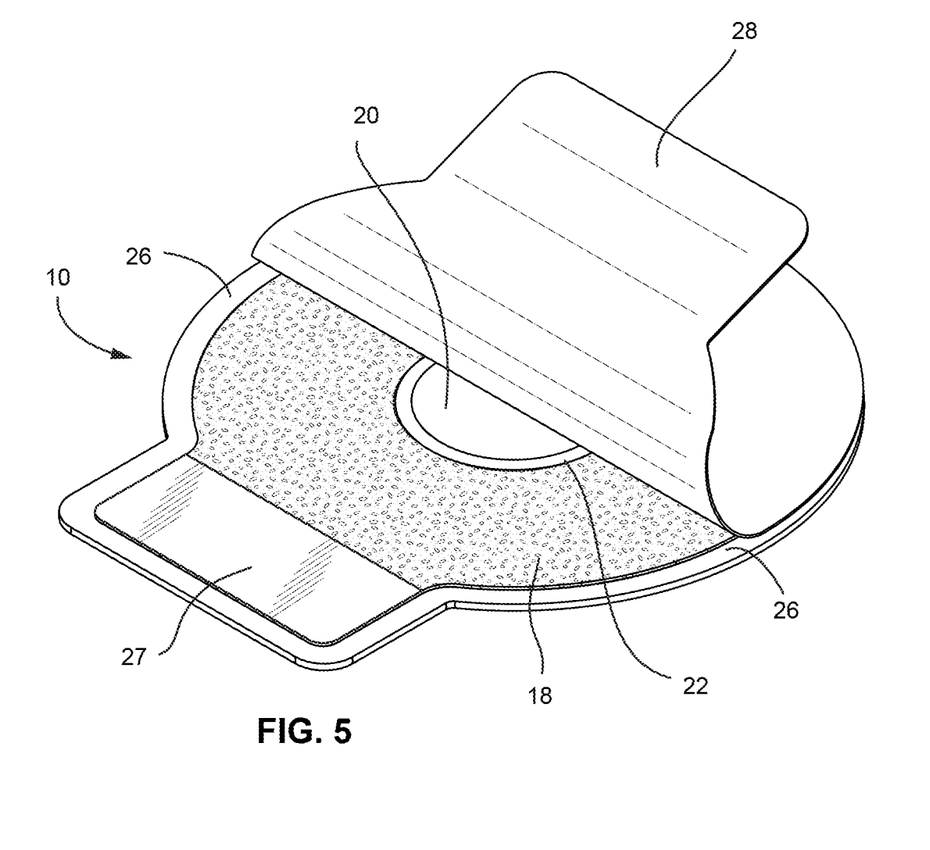
FIG. 5 is a perspective view of the bottom of the medical dressing, showing the release liner partially peeled from the main disc.

FIG. 2 shows a top view of the medical dressing 10, FIG. 3 shows a bottom (adhesive side) view of the medical dressing 10, FIG. 4 shows a perspective view of the top of the medical dressing 10 and FIG. 5 shows a perspective view of the bottom of the medical dressing 10. The medical dressing 10 may be formed of a pair of flexible, thin plastic membranes, e.g., sheets, which include a main membrane 12 and a sealing membrane 14. The membranes may be a transparent or translucent such that the chest and wound are visible while the dressing is applied to the wound 102.

The main membrane 12 includes a front (skin side) surface 16 configured to face a chest of a patient and a back surface opposite to the front surface. The front surface is substantially coated in its entirety with an adhesive layer 18. The flexible main membrane includes a center opening 20. The center opening 20 may be circular, oval, curvilinear in shape, rectangular or have some other shape. The diameter or other dimension from one side of the opening to the other may be one inch, one and one-half inches, two inches, two and one-half inches or other diameter selected to extend around the wound or anticipated wound dimensions. The opening 20 should be centered on the wound 102 when the dressing 10 is applied to the skin on the chest of the patient. The opening 20 may have an area sufficiently greater than the puncture so that the edges of the puncture are not coated with the adhesive of the dressing. The opening 20 is intended to allow air in the pleura space to vent from the wound and through the opening.

An annular ring 22 (34 for opposite surface) on the front surface 16 of the dressing 10 is devoid of adhesive and extends from the outer perimeter of the opening 20 to the inner edge of the adhesive surrounding the opening. The annular ring 22 assists in preventing adhesive from creeping around the edge of the opening 20 and onto the back side The annular ring 22 also serves as a seat surface that allows contact between the main membrane and the flexible sealing membrane. The annular ring may have a width (from the opening to the adhesive layer) of one-eighth of an inch to one-quarter of an inch. The annular ring is a region of the main membrane, but may be a structural ring having minimal height, e.g., less than one-eighth of an inch.

An annular perimeter region 26 on the front surface 16 of the main membrane is also devoid of adhesive. The annular perimeter region 26 may extend entirely around the perimeter of the main membrane. The annular perimeter region may assist in preventing adhesive from creeping from between the main membrane and the skin and limits contact between the adhesive potential contaminants that may be present around the application area. The annular perimeter region 26 also facilitates device removal when other portions of the device, such as the tab, are inoperable or inaccessible.

The adhesive layer 18 may be a biocompatible adhesive disposed for securing the main membrane 12 to a patient's skin. Suitable adhesives for adhering the flange body to the patient's skin include hydro gel, acrylic, silicone gel, silicone PSA or hydrocolloid. The adhesive layer 18 may include a substrate layer that is coated on both sides with adhesives. The substrate provides support for the adhesives. A release liner (membrane) 28 (shown in FIG. 5) covers the adhesive layer until the medical dressing 10 is to be applied to the skin of the chest. The release liner 28 is then peeled from the dressing and the exposed adhesive layer is applied to the skin as the dressing is pressed to the skin while the opening 20 of the dressing is aligned with the wound.

A rectangular tab section 27 on the main membrane and adhesive layer provides a grip for removing the medical dressing from the skin. The adhesive portion of the tab 27 section may be covered by additional non-adhesive material on both sides by sheets to prevent the adhesive from adhering to the skin or to the release liner 28, which covers the adhesive layer 18. The release membrane is removed to expose the adhesive layer and just before the medical dressing is applied to the skin of the chest and over the puncture wound. However, the tab 27 section may continue to be covered with the non-adhesive to facilitate the later removal of the dressing.

The sealing membrane 14 is superimposed on a back surface 17 of the main membrane 12. The sealing membrane 14 may be a circular disc and have a diameter about twice, e.g., between 1.5 to 2.5 times, the diameter of the opening 20. For example, the diameter of the sealing membrane 14 may be three and one-half inches, four inches or four and one-half inches. The sealing membrane 14 covers the opening 20 and the puncture wound 102. The sealing membrane 14 is an impermeable membrane and as such prevents air, water, dirt and other material from entering the wound.

The sealing membrane 14 is joined to the main membrane by an annular array of joints 30. The joints 30 are regions where the sealing membrane is joined to the main membrane. The joints 30 may be arch shaped. The length of each joint may be equal to the length of the vent passage adjacent the joint. The length of the joint is the distance from an inner perimeter to an outer perimeter of the annular array of joints.

The joints 30 may be arranged to form an annulus around the opening 20. The joints 30 may be formed by welding or otherwise fusing the sealing membrane to the main membrane, by an adhesive layer or by other joining technique. The annular array of joints seal the sealing membrane to the main membrane. The joints 30 cause the sealing membrane and main membrane to be an integral, single component that forms the medical dressing 10.

Several different methods of adhesion may be used to secure sealing membrane 14 to the main membrane; one method of joining the materials is radio frequency (RF) or high frequency welding. These welds are both permanent and highly durable. One style of adhesion that forms the welds between sealing membrane 14 and the main membrane employs a method of joining thin sheets of polar thermoplastic material together using high frequency (10 to 100 MHz) electromagnetic energy to excite, heat and fuse the materials. Because plastic welding uses a process of creating a molecular bond between two compatible thermoplastics, no additional materials are needed, which allows for the maintenance of the minimizes height profile of the device. In addition, RF welding offers superior strength, and often drastically reduced cycle times, to mechanical joining or chemical bonding using adhesives.

Vent passages 32 are sandwiched between the main membrane and the sealing membrane. The vent passages extend between adjacent joints 30. The vent passages define an air passage extending from the opening 20 and an outer edge, e.g. perimeter, of the sealing membrane. The vent passages allow air from the chest wound to vent from the wound to the atmosphere. The vent passage expands into an air conductive passage while the air pressure above atmospheric pressure at the wound and immediately below the sealing membrane. The above atmospheric pressure causes the sealing membrane to deflect upward above the opening and above the vent passages. While the vent passages 32 are expanded, air vents from the wound to allow air to vent from the pleura space. By venting air from the pleura space, the lungs of the patient can further inflate so that the patient can better breath.

The number of vent passages 32 may be five, six or more. Because of the large number of vent passages, one or more of the vent passages may clog, such as with blood, while other passages continue to expand and allow venting of air from the chest wound. The width and length of each vent passage 32 may be selected to be sufficiently long and narrow to ensure that the passage collapses and prevents air conveyance when the air pressure at the wound is at or below atmospheric pressure. A competing and contrary requirement is that the vent passage should be short and wide to avoid being clogged with blood and debris and to air readily vent from the wound with minimal resistance due to the vent passage. Balancing these competing requirements is preferred to achieve an optimal vent passage.

In one embodiment, the dimensions of the vent passage may be one-half to one and a quarter inch in length, with a lengths of three-quarters and one an inch being particularly useful. The width of the vent passage may be one tenth to one quarter of an inch, with a width of one quarter of an inch being particularly useful. The ratio of length to width of the air passage may be used as an indicator of a vent passage that balances the needs to prevent air entering the wound, allowing air to vent from the wound and reducing the risk that the passage becomes clogged with blood or other material. A ratio length to width in a range of 2 to 8, such as 4, may be optimal for balancing these needs.

Figure 6:
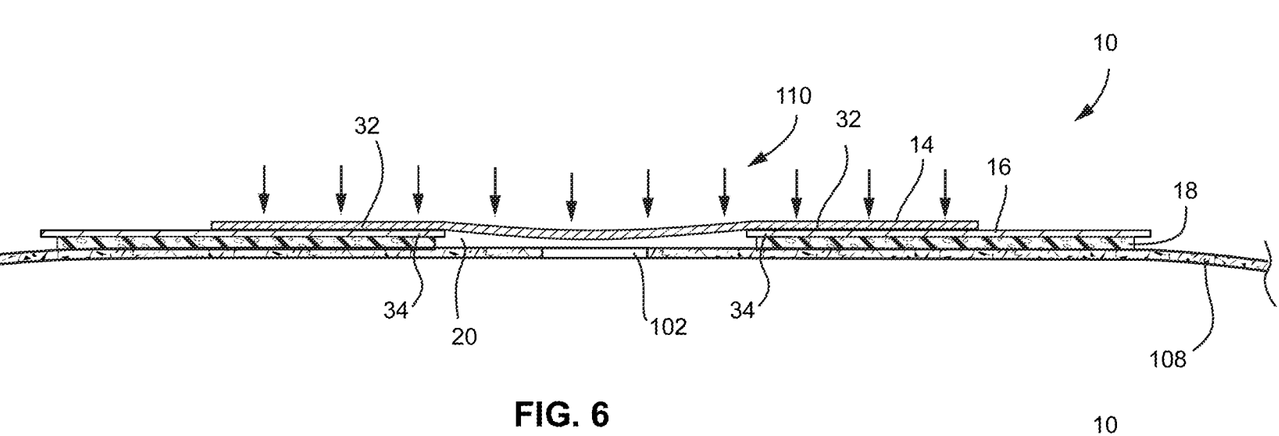
FIG. 6 shows a cross-section of the medical dressing along line A-A in FIG. 2, while the vent passages are closed.
Figure 7:
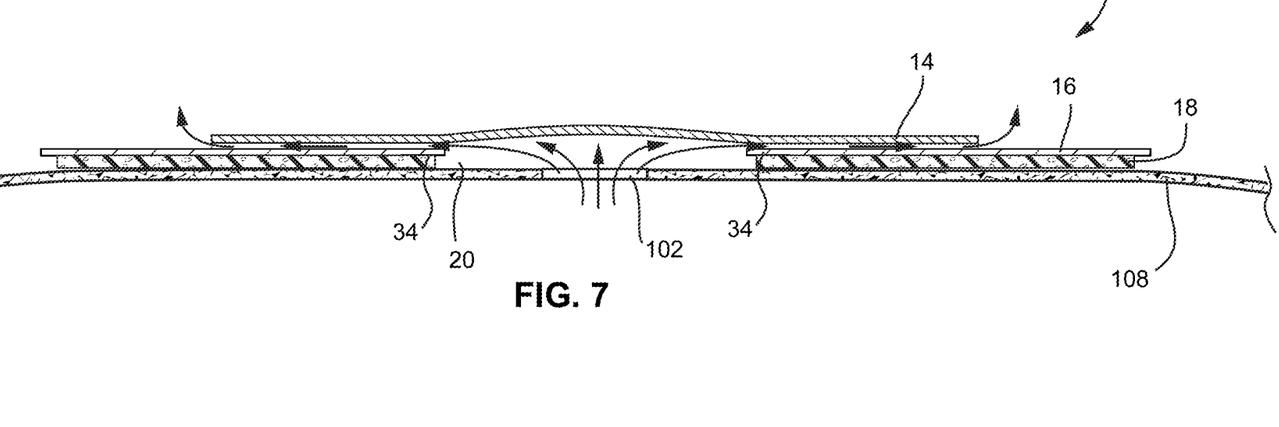
FIG. 7 shows a cross-section of the medical dressing along line A-A in FIG. 2, while the vent passages are open.

FIGS. 6 and 7 shown the medical dressing 10 in cross section. The dressing 10 is applied to the skin 108 and is centered on the wound 102. Atmospheric air 110 (FIG. 6) deflects the sealing membrane 14 against the main membrane 12. The pressure of the atmospheric air is greater than the pressure of the air immediately above the wound and between the wound and the sealing membrane. While the atmospheric air pressure is greater than the wound air pressure, the sealing membrane is deflected towards the wound and seals against the main membrane. In particular, the sealing membrane is pressed against an annular ring 34 (22 on the opposite surface) on the back surface of the main membrane 12. The annular ring 34 is between the perimeter of the opening 20 and the inner perimeter of the annular array of joints 30. The annular ring 34 is a flat surface that forms a seal with the sealing membrane when the atmospheric pressure is greater than the pressure at the wound. Similarly, the atmospheric pressure being greater than the wound pressure causes the sealing membrane 14 to press against the main membrane 12 along portions or the entire length of each of the vent passages 32. The seals formed between the sealing membrane 14 and the main membrane 12 prevent air from passing from the atmosphere into the wound. The annular ring 34 may have a width of between one quarter to one eight of an inch. Additionally, the annular ring may be set away from the weld of the dressing by a width of one quarter to one-half of an inch.

FIG. 7 shows by dotted lines with arrows the air pressure at the wound being greater than the atmospheric pressure. The air pressure at the wound deforms the sealing membrane away from the wound and away from the main membrane. This deformation unseals the sealing membrane from the main membrane at the annular ring 34 of the main membrane and along the vent passages 32. Because of the unsealing, air is evacuated from the wound to atmosphere. Evacuating the air from the wound also evacuates air from the pleura space, which reduces the air pressure in the pleura space. A reduced pressure in the pleura space allows the lungs to expand as the patient inhales and thus allows the patient to breath by restoring proper lung mechanics.

The maximum height of each of the vent passages 32 may be less than one sixteenth of an inch or less than one thirty-second of an inch. The vent passages 32 may have a height only when there is an above atmospheric pressure in the passage and have no height, i.e. be closed, when the pressure in the passage and at the wound is at or below atmospheric pressure. Thus, the vent passages are configured to be closed and prevent air entering the opening 20 and the wound. The vent passage need not be closed along the entirety of its length. It should be sufficient, for most applications, that the vent passage closes at one or more positions along its length so as to prevent air traveling through the passage towards the opening.

Figure 8:
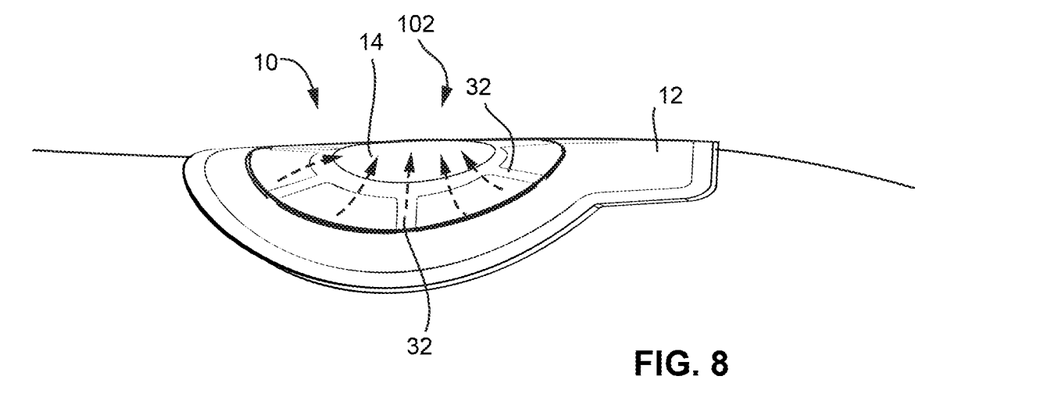
FIGS. 8, 9 and 10 show a sequence of operation of the medical dressing when applied to a sucking chest wound.
Figure 9:
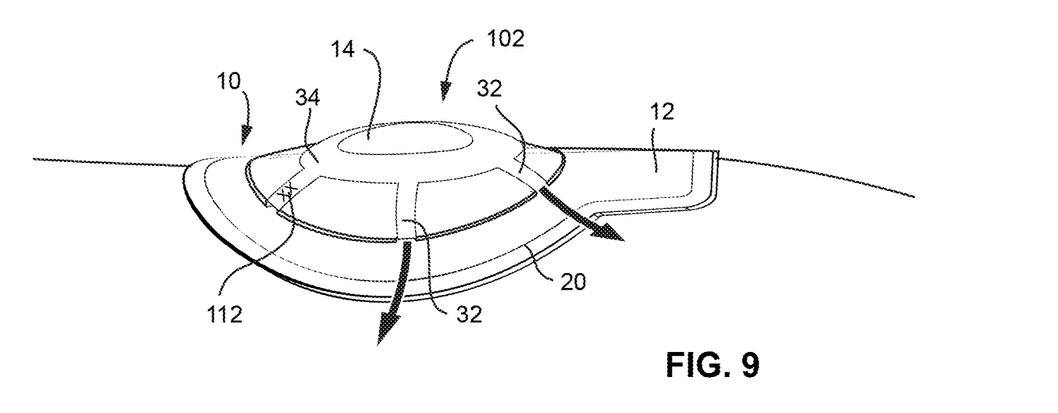
Figure 10:
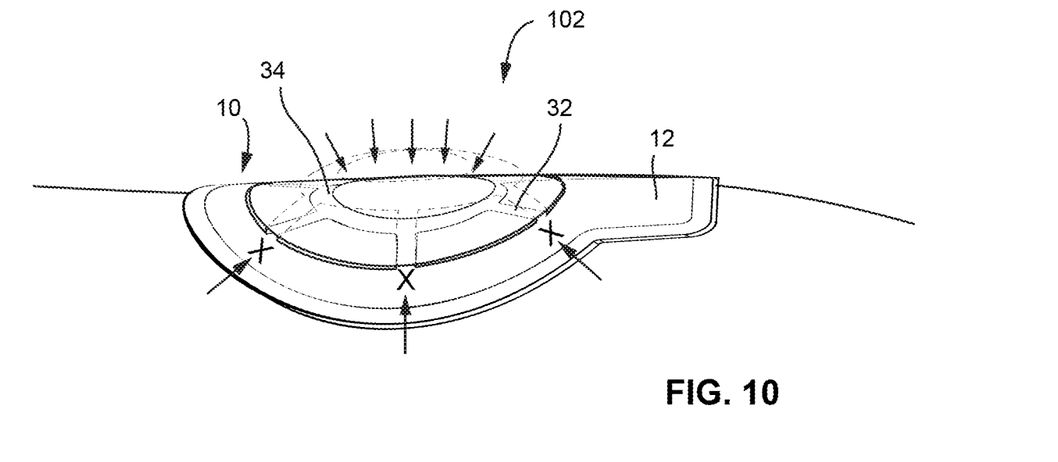

FIGS. 8, 9 and 10 illustrate the operation of the medical dressing 10. In FIG. 8, as air (see dotted lines) escapes from the wound, the air pushes out on the sealing membrane 14 and deflects that membrane away from the main membrane 12 to open the vent passages 32. FIG. 9 shows the sealing membrane 14 deflected away from the main membrane 12, such that the ring 34 of the main membrane is un-sealed from the sealing membrane and the vent passages 32 are open. This allows air to be evacuated from the wound. One of the vent passages may be occluded 112 with blood, fluid, or other debris, as shown in FIG. 9. The occlusion 112 prevents air passing through one vent passage. There are other open vent passages 32 for air (solid line arrows) to pass through and evacuate from the lung, minimizing the effect of the vent and device occlusion 112. The number of vent passages and the cross sectional area of the remaining open passages are sufficient that one, two or more passages may be occluded while the medical dressing 10 operates sufficiently to allow air to evacuate from the wound. In addition, as the vents are configured to extend radially away from the center of the dressing, the vent passages 32 are distributed at the greatest distance from one another, further reducing the risk of total device occlusion.

FIG. 10 shows the external air pressure (see dotted lines with arrows) becoming greater than the pressure at the surface of the wound. As the external air pressure becomes greater, the sealing membrane 13 is pressed down against the main membrane 12 such that the vent passages 32 are closed. The closing of the vent passages prevents air (solid line arrows) from passing through the vent passages and entering the wound. It is during this time that the lungs are able to expand within the seal pleural space. In combination, the opening and closing of the vent passages restore the complex lung mechanics that allow the lung to expand and contract within the pleural space.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention is:

1. A medical dressing configured to be applied to a chest wound, the dressing comprising:
  a flexible main membrane including a front surface configured to face a chest of a patient and a back surface opposite to the front surface, wherein the flexible main membrane includes an opening;
  an adhesive layer on the front surface of the flexible main membrane wherein the adhesive layer extends entirely around the opening;
  a flexible sealing membrane entirely covering the opening of the flexible main membrane and overlapping at least a portion of the flexible main membrane;
  an annular array of joints sandwiched between the sealing membrane and the flexible main membrane, wherein the annular array of joints extends around the opening; and
  vent passages sandwiched between the flexible main membrane and the sealing membrane, wherein the vent passages each extend between an adjacent pair of the joints and defines an air passage extending from the opening to an outer edge of the sealing membrane.

2. The medical dressing of claim 1 wherein the vent passages are at least six in number.

3. The medical dressing of claim 1 wherein the vent passages extend radially from the opening and are arranged symmetrically around the opening.

4. The medical dressing of claim 1 wherein the sealing membrane includes a circular outer perimeter having a diameter of three to five inches.

5. The medical dressing of claim 1 wherein the vent passages each are straight passages having straight sides along their lengths.

6. The medical dressing of claim 1 wherein the annular array of joints are welds between the flexible main membrane and the sealing membrane.

7. The medical dressing of claim 1 wherein the opening has a diameter of 0.5 to 2 inches, the sealing membrane has a diameter of 2.5 to 3 inches, and the flexible main membrane has a diameter of 4 to 6 inches.

8. The medical dressing of claim 1 wherein the air passage defined by each of the vent passages is configured to close when a pressure at the opening is at or below atmospheric pressure.

9. The medical dressing of claim 1 wherein a ratio of a length to width to each of the vent passages is in a range of 3 to 5.

10. The medical dressing of claim 1 wherein each of the vent passages has a length of between 0.75 of an inch to 1.5 of an inch.

11. The medical dressing of claim 1 further comprising an annular ring devoid of adhesive layer on the back surface of the flexible main membrane, wherein the annular ring extends widthwise from an outer edge of the opening to an inner perimeter of the annular array of joints, and the annular ring has a width of 0.25 to 0.1 of an inch.

12. The medical dressing of claim 11 further comprising an annular ring devoid of the adhesive layer on the back surface of the flexible main membrane, wherein the annular ring extends widthwise from an outer edge of the opening to an inner perimeter of the annular array of joints, and the annular ring has a width of 0.25 to 0.1 of an inch.

13. A medical dressing configured to be applied to a chest wound, the dressing comprising:
  a flexible main membrane including a front surface configured to face a chest of a patient and a back surface opposite to the front surface, wherein the flexible main membrane includes an opening;
  an adhesive layer on the front surface of the flexible main membrane wherein the adhesive layer extends entirely around the opening and is offset from the opening by at least one-eighth of an inch;
  a flexible sealing membrane entirely covering the opening of the flexible main membrane and overlapping at least a portion of the flexible main membrane;
  an array of joints sandwiched between the sealing membrane and the flexible main membrane, wherein the array of joints extends around the opening of the flexible main membrane, and vent passages sandwiched between the flexible main membrane and the sealing membrane, wherein the vent passages extend between joints in the array of joints and each of the vent passages defines an air passage extending from the opening to an outer edge of the sealing membrane.

14. The medical dressing of claim 13 wherein the vent passages are at least six in number.

15. The medical dressing of claim 13 wherein the vent passages extend radially from the opening and are arranged symmetrically around the opening.

16. The medical dressing of claim 13 wherein the sealing membrane includes a circular outer perimeter having a diameter of three to five inches.

17. The medical dressing of claim 13 wherein a ratio of a length to width to each of the vent passages is in a range of 3 to 5.

18. The medical dressing of claim 13 wherein each of the vent passages has a length of between 0.75 of an inch to 1.5 of an inch.

* * * * *